United States Patent [19]

Atkinson

[11] Patent Number: 5,013,551

[45] Date of Patent: May 7, 1991

[54] ANIMAL REPELLANT LLDPE

[75] Inventor: Charles E. Atkinson, Orange, Tex.

[73] Assignee: E. I. Du Pont de Nemours and Company, Wilmington, Del.

[21] Appl. No.: 473,684

[22] Filed: Feb. 1, 1990

[51] Int. Cl.$^5$ ............................................ A01N 25/34
[52] U.S. Cl. ................................... 424/412; 424/405; 428/34.3
[58] Field of Search ................................ 424/405, 412

[56] References Cited

U.S. PATENT DOCUMENTS 4,320,112  3/1982  Jones et al. ........................... 424/19
4,795,665  1/1989  Lancaster ............................ 428/34.2

FOREIGN PATENT DOCUMENTS

2542002A1  9/1984  France .

Primary Examiner—Thurman Page
Assistant Examiner—D. Gabrielle Phelan

[57] ABSTRACT

Trash bags and other products from LLDPE are made animal repellent by incorporation of terpene in the LLDPE in the melt process for fabricating such products from the polymer.

15 Claims, No Drawings

ANIMAL REPELLANT LLDPE

BACKGROUND OF THE INVENTION

This invention relates to the incorporation of terpene into molten LLDPE for achieving animal repellent articles formed from the resultant melt.

French Patent 2,542,002 (1984) discloses the incorporation of terpene into a wide variety of thermoplastic and thermosetting polymers for the purpose of modifying the olfactory effect of the polymer so as to have a repulsive effect on animals. Various amounts of terpene additive are disclosed, i.e. 0.01 to 5% by wt., and most frequently between 0.1 and 2%. In order to mask the strong odor of products in a package (case) made from the polymer, the best percentages of terpineol is in the range of 0.5 to 1.5 % of the weight of the package. Example 1 discloses the manufacture of trash bags from LDPE, in which 1% by weight of a mixture of terpineol and heavy terpene was added to low density polyethylene (LDPE) molding granules for extrusion into film which is fabricated into trash bags. The resultant trash bags are disclosed to be filled with odorous foodstuff and they were observed not to be attacked by dogs, cats and rats, whereas trash bags made from the LDPE without the terpene additive were observed to be attacked by the animals.

Unfortunately, the trash bags of Example 1 of the French patent have insufficient shelf life to be of practical utility. The volatility of the terpene additive in the LDPE rapidly decreases the amount of terpene present in the trash bag until it is no longer effective. The amount of terpene added in Example 1 of the patent appears to have been limited so as not to cause any defect in the film formed from the terpene/LDPE mixture. Another limitation on terpene amount would be to avoid excess terpene which would have an offensive odor to humans or would provide an offensive oily appearance to the film.

U.S. Pat. No. 4,320,112 discloses animal and insect repellent trash bags in which the combination of naphthalene flakes and oil of citronella in solid form is added to a synthetic resin forming the bags. The patent discloses that each component of the combination is insect repellent and that the combination provides animal repellency as well. The patent also discloses that the weight proportion of naphthalene to oil of citronella is at least 4:1. The use of these additives in solid form inevitably weakens the bag because there is no compatibility between the resin and these additives, whereby they form weak spots for the development and propagation of tears in the film forming the trash bag. Thicker films can compensate for this deficiency, to provide for the strength needed by trash bags made from the film, but this is uneconomical.

SUMMARY OF THE INVENTION

It has been discovered that terpene can be incorporated in a greater amount in LLDPE as compared to LDPE to provide greater animal repellent effectiveness in articles formed from the LLDPE. Unexpectedly, the LLDPE is capable of holding up to about 2.5 percent based on the total weight of the mixture of terpene plus LLDPE before its presence as an odor characteristic of the terpene is detectable by humans and an even greater proportion without being noxious to humans and without detracting from the strength of articles formed from the mixture. The presence of the greater proportion terpene in the article provides an extended shelf life for the articles and thus, more effective repulsion of animals. The presence of the greater proportion of terpene in LLDPE presents a larger dose of the terpene to the animal which gnaws on the article, and this has been observed to deter the animal from further attack on any LLDPE article containing the terpene. Thus, if the odor of the LLDPE article containing the terpene does not repel the animal, then one taste of the article appears to condition the animal to avoid either further attack on the article or fresh attack on other articles containing the terpene.

Therefore, the present invention in one embodiment resides in the conventional process of forming articles from a melt of LLDPE, with the improvement being the incorporation of terpene in the melt in an amount effective to repel animals in the resultant article.

In another embodiment of the present invention, the article is in the form of a film, and a preferred form of the film is a trash bag thereof. Testing of trash bags of the present invention has demonstrated effective repulsion of animals from the bags and thus from access to the foodstuff contents thereof.

DETAILED DESCRIPTION OF THE INVENTION

The LLDPE as understood in the art, is linear low density polyethylene. It is also a copolymer, instead of a homopolymer. Thus, it is a copolymer of ethylene with at least one monomer selected from $C_4$ to $C_{10}$ alpha monoolefins such as 1-butene and 1-octene, in which the molecules of the copolymer comprises long chains with few side chain branches, in contrast to LDPE which is a much more highly branched low density ethylene homopolymer. The LLDPE generally has a density from about 0.91 g/cc to 0.935 g/cc. especially for film-making purposes and depending on the proportion of $C_4$ to $C_{10}$ alpha-monoolefin present in the copolymer. Generally, the copolymer will contain 2 to 15% of the alpha-monoolefin comonomer based on the weight of the copolymer and will have a melt flow index of 0.01 to 20 g/10 min.

The LLDPE available in the art oommonly has slip and anti-block agents incorporated therein so that film formed therefrom can be rolled up and unrolled for forming into articles such as trash bags and the resultant bags can be handled for packaging. It has been observed that the presence of the terpene in LLDPE film made in accordance with the present invention has improved slip and anti-block character.

The terpene incorporated into the LLDPE in accordance with the present invention is a material chemically comprising isoprene units (5 carbon atoms) arranged head-to-tail fashion, which may be acyclic, monocyclic, bicyclic, tricyclic, etc., depending on the number of isoprene units present. The terpene may be unsaturated, saturated or partially saturated. Sometimes the terpenes are referred to as isoprene oligomers. They are available from nature, such as from pine trees and citrus fruit, or they can be synthesized to chemically resemble terpenes derived from nature. The terpenes include derivatives of the isoprene oligomers, such derivatives including alcohols, aldehydes, and esters, such derivatives being commonly referred to as terpenoids. Commercially available terpenes are generally in the form of mixtures of a plurality of terpene compounds.

Regardless of the isoprene oligomer size or the source of the terpene or its purity in the sense of whether a single terpene or mixture thereof, it should exhibit taste and odor properties which are noxious to animals. Thus, if the odor of the terpene emanating from the LLDPE article does not repel the animal, the taste of the terpene when the animal bites into the article will repel the animal. Preferably the odor of the terpene is not noxious to humans. This is generally achievable by terpenes by virtue of the greater sensitivity of the sense of smell of animals, whereby an amount of terpene in the LLDPE article can be chosen which satisfies this differential sensitivity to achieve animal repellency without being repulsive to humans.

Preferably, the terpene is also normally liquid, ie., liquid at room temperature, e.g. 18° to 20° C., which enables a complete and uniform distribution of the terpene within the molding granules of LLDPE to be made prior to melting within the extruder. The terpene may be a mixture of terpenes, with sufficient low melting terpene being present in the mixture to impart normal liquidity to the terpene incorporated into the LLDPE. In place of low melting terpene, a small amount of organic solvent for the terpene can be used, e.g. 2 to 5% based on the weight of terpene plus solvent, to provide normal liquidity to the terpene.

Another preferable characteristic of terpenes used in the present invention is that they have a high boiling point relative to the extrusion temperature of the LLDPE. This minimizes or prevents gassing of the terpene within the extruder and within the LLDPE extrudate from the extruder. Thus, a boiling point of at least 175° C., and more preferably, at least 200° C. is preferred for the terpenes used in the present invention.

Within these parameters, the terpene can be selected from a large group of compounds within the terpene family, especially the monoterpenes having the general formula $C_{10}H_{16}$, such as bornylene, camphene, carene, dipentene, fenchene, geranene, limonene, myrcene, ocimene, phellandrene, pinene, sabinene, sylvestrene, terpinene, and thiyene; sesquiterpenes having the general formula $C_{15}H_{24}$, such as cadinene, cannibene, carophyllene, cediene, clovene, guajene, patchoulene, santalene, selinene, and zingiberene; and diterpenes having the general formula $C_{20}H_{32}$, such as isophytol and steviol. Examples of terpenoids include terpineol of the formula $C_{10}H_{18}O$, either the alpha, beta, or gamma forms having boiling points of 210° C. and above, fenchol and borneol, dihydrochloride of the formula $C_{10}H_{16}2HCl$, halogenated terpene such as the hydroiodide $C_{10}H_{16}HI_1$, and terpenol of the formula $C_{10}H_{17}OH$.

LLDPE is formed into articles by a conventional process such as extrusion, which first melts the LLDPE, generally supplied to the process as molding granules, and then extrudes the melt through a die in the shape desired, such as a film. Thereafter, the film may be stretched under molecular orientation conditions to decrease the film thickness and increase its strength.

In accordance with the present invention, the terpene can be incorporated into the LLDPE melt by mixing with the LLDPE molding granules prior to their melting so as to obtain a uniform distribution of the terpene within the resultant LLDPE article. This can be accomplished by tumbling the granules with the terpene, preferably in liquid form, so that it coats the surface of the granules. Subsequent melting of the so-coated molding granules within the extruder confines any volatilized terpene within the melt, and very little terpene, if any, is lost as the extrudate exits the extrusion die because of the rapid cooling of the extrudate as it enters cool air or water quench. Another method for incorporating terpene into the LLDPE melt is to inject the terpene into the extruder already processing the LLDPE for extrusion into molding granules or the article desired.

The amount of terpene added to the LLDPE will depend on the particular terpene, including mixture thereof, selected to provide the animal repellent effect desired in the article formed therefrom, while at the same time not having a noxious aroma to humans. Thus, the loading of the terpene can be high enough, e.g. 3.5 to 6% by weight, in the LLDPE that animal is repelled from gnawing at the LLDPE article. At low loadings, e.g., 2.2 to 3.4% by wt., the animal may gnaw at the article and then be repelled therefrom by the taste of the terpene, present in sufficient amount to present this distaste to the animal. Thus, the proportion of terpene added to the LLDPE molding granules will generally be within the range of 2.2 to 6% by wt., and preferably 3.0 to 4.0% by wt., based on the total weight of the LLDPE and terpene.

The ability of the LLDPE to "swallow up" these relatively high levels of terpene provides a slower release of the aroma of the terpene; this together with the high loading of the terpene in the polymer gives the article molded from the polymer an extended shelf life. The terpene, as a mixture, can also be adjusted for the climate of the use of the article. For cold climate use, lower boiling terpene can predominate, because the cold temperature will minimize volatilization from the article. For warm climate utility, higher boiling terpene can predominate, which minimizes volatilization. In either case, the presence of higher boiling terpene gives long lasting animal repellent effect, while lower boiling terpene gives the aroma which tends to deter the animal from attacking the LLDPE article in the first place.

A particularly valuable utility for LLDPE articles made in accordance with the present invention is trash bags, which can be formed by conventional means from extruded film of the LLDPE/terpene mixture. Typically, the thickness of the film used to make trash bags will be on the order of 1.0 to 1.5 mil (0.025 to 0.038 mm), these small thicknesses indicating that the terpene additive to the LLDPE does not adversely effect the strength of the trash bag. The extended life of the animal repellent effect in articles made from melts of LLDPE in accordance with the process of the present invention also make the present invention applicable to forming such articles as trash containers, cable coatings and piping especially for underground use, and as film ground-cover (perforated to permit the growth of vegetation) for areas desired to be free of animals. The process of the present invention may also be practiced as an extrusion of a coating of the LLDPE onto a preformed substrate or coextrusion with a thermoplastic resin to form useful articles such as bags for animal feed, in which an inner layer provides barrier properties to the bag for feed preservation purposes and an outer layer of the LLDPE containing terpene serves to prevent rodent attack during storage of the bags of feed. The present invention also provides the versatility of the article made from the LLDPE melt being molding granules, which can then be used in subsequent thermoplastic plastics such as extrusion or injection molding to form a wide variety of articles such as described above.

Examples of the invention are as follows (parts and percents by weight unless otherwise indicated):

a. To molding granules of LLDPE was added a 50:50 (by volume) mixture of liquid monoterpenoid, viz alpha-terpineol (taken from the light end of the distillation process for refining oils) and liquid sesquiterpene (taken from the heavy end of the distillation process) available from TR-Metro Chemicals as Oil M. The LLDPE was a copolymer of ethylene with 6.6% of butene co-monomer, based on the weight of the copolymer, and it had a density of 0.918 g/cc and melt flow index of 1.0 g/10 min. The alpha terpineol and sesquiterpene both were extracts from pine tree rosin, had pine scent, and had boiling ranges of 210° to 215° C., and 185° to 335° C., respectively, and the mixture of these terpenes totalled 2.0, 2.5, 3.0, 3.5 and 4.0% based on the weight of the copolymer plus terpene mixture, in separate experiments. The overall mixture was mixed for 30 minutes, at which time the molding granules all appeared to be wet by the terpene mixture. The resultant mixture was fed into an extruder for melting the LLDPE in the mixture, and the extrusion temperature as the mixture entered the extrusion date was 240° C., which exceeded the melting point of the LLDPE but was not so high as to cause gassing of the terpenes as the extrudate exited from the extrusion die. A terpene odor was detectable at the extrusion die, but little terpene was lost from the LLDPE as indicated by the absence of any oil residue on the surface of the chilled water quench bath into which the extrudate was passed, and the extrudate was cut into molding granules for subsequent molding of articles. Little of the terpene is lost in the extrusion process because of the high boiling points of the terpenes used and the rapidity with which the extrudate achieves a temperature below these terpene boiling points after extrusion.

b. At the 2.0% terpene level in the molding granules, the molding granules exhibited no terpene odor, indicating that the LLDPE had completely "swallowed up" the amount of terpene and that this low loading amount was probably not adequate for repelling animals, especially if the article molded from the molding granules was to be subjected to storage and/or heat prior to use and was to be thin-walled such as in the case of a trash bag, whereby some of the terpene would volatize and be unavailable for the repellent function. The odor from the molding granules having the higher loadings of terpene exhibited increasingly strong odor with increasing amount of terpene even at the 4.0% concentration, the odor was pleasant to human scent, suggesting a quality of freshness which is characteristic of the pine odor of these terpenes. None of the molding granules had an unpleasant oily appearance; i.e., there was no visible evidence that terpene was present in the molding granules.

c. The molding granules containing 3.5 wt. % terpene was extruded, using a bag extruder, into trash bags 0.038 mm (1.5 mil) thick and measuring 40.6 cm × 35.6 × 91.4 cm (16 in × 14 in × 36 in). The bags had a terpene odor but did not exhibit any oily feel or appearance. The bags were tested for animal repellency in accordance with the following procedure:
  (i) Trash bags of the same LLDPE and same dimensions but without any terpene additive were made (control bags).
  (ii) A group of dogs were each fed a daily diet of 450 g. of a 70%/30% mixture of ground beef and dry dog food for about one week, with the feeding being carried out with the food mixture being contained in a control bag for each dog to condition the dogs to the habit of tearing through the trash bag for its food.
  (iii) Groups of one to three dogs were admitted to the same feeding area, but this time containing three control bags and three trash bags of the present invention made as described above, each bag containing 450 g of the food mixture described above. The results were approximately the same, whether one dog or three dogs were present. All of the food was consumed from the three control bags, while the three trash bags of the present invention were left virtually unharmed. Sometimes one of the dogs would break into one of the trash bags of the present invention and consume only a portion of its food content before being repelled by the terpene odor and taste. Such dogs would then shy away from future attack on trash bags of the present invention used in the test.
  (iv) This test was repeated in a community in which trash bags were subjected to attack by a wide variety of animals, e.g., dogs, cats, raccoons, possums, and rodents, but using household trash instead of a special food content, and placing the trash bags (some control bags and some trash bags of the present invention) in the usual outdoor garbage collection areas. Often the control bags were torn open and the contents widely scattered by foraging animals. Many fewer trash bags of the present invention showed evidence of any animal attack and none of them were torn open sufficiently for contents to be removed and scattered by the foraging animals. Similar results are expected at higher loadings of terpene when the bags are to be stored or used in a hot climate and at lower loadings of terpene, down to 2.2% by weight, when the bags are used in a cooler climate.
  (v) Trash bags of the present invention which were tested as described above about six months after manufacture were just as effective as such trash bags tested promptly after manufacture, demonstrating the shelf life available for articles made in accordance with the present invention.
  (vi) The tensile strength of control bags and trash bags of the present invention was tested, with the result being an average of 3816 psi and 3951 psi respectively, demonstrating no appreciable adverse affect of the terpene additive on the strength of the article molded therefrom.

d. Trash bags having a 17.8 mm wall thickness were made from LDPE having a density of 0.917 g/cc, using both 1% by weight and 2% by weight of alpha-terpineol, based on the total weight of LDPE and terpene. After 30 to 45 days of storage, the bags exhibited no discernible animal repellency as compared by trash bags containing no terpene in the bag wall. The bags containing 2% by weight of terpene were oily in appearance and thus were offensive to human handling.

e. The experiment of paragraph d. was repeated except that the terpene level was increased to 2.25% based on total weight of terpene plus LDPE and the wall thickness of the bag was increased to 0.04 mm in an attempt to increase the effectiveness of LDPE especially after storage before use. The result was that the bags exhibited the undesirable oily appearance and a terpene odor so strong that it was repugnant to many humans, making these bags be unsuitable for use.

As many widely different embodiments of this invention may be made without departing from the spirit and scope thereof, it is to be understood that this invention is not limited to the specific embodiments thereof except as defined in the appended Claims.

What is claimed is:

1. In the process of forming articles from a melt of LLDPE, wherein said LLDPE is a linear low density polyethylene which is a copolymer of ethylene with at least one monomer selected from the group consisting of $C_4$ to $C_{10}$ alpha monoolefins, wherein the low density of said LLDPE is about 0.91 to 0.935 g/cc the improvement comprising incorporating terpene into said melt in an amount effective to repel animals in the resultant article.

2. In the process of claim 1 wherein the amount of said terpene is at least 2.2% based on total weight.

3. In the process of claim 2 wherein no more than 6% based on total weight of the terpene is present.

4. In the process of claim 1 wherein the terpene is a mixture of terpenes of differing boiling points.

5. In the process of claim 1 wherein the terpene is monoterpenoid having the general formula $C_{10}H_{18}O$ or sesquiterpene having the general formula $C_{15}H_{24}$ or mixture thereof.

6. In the process of claim 1 wherein the terpene is liquid.

7. In the process of claim 1 wherein the terpene has a pine scent.

8. The articles of claim 1 wherein the terpene has a boiling point of at least 175° C.

9. Film made by the process of claim 1.

10. Trash bag made from the film of claim 9.

11. LLDPE film containing from 2.2 to 6% terpene based on total weight, said LLDPE being a linear low density polyethylene which is a copolymer of ethylene with at least one monomer selected from the group consisting of $C_4$ to $C_{10}$ alpha monoolefins.

12. The film of claim 11 wherein the amount of terpene present is from 3.0 to 4.0% by weight.

13. In the process of claim 1 wherein the low density of said LLDPE is about 0.91 to 0.935 g/cc and from 2 to 15 wt. % of LLDPE is composed of said alpha monoolefin.

14. In the process of forming trash bags from a melt of linear low density polyethylene, the improvement comprising incorporating terpene at no more than 6% based on the total weight to repel animals from the resultant trash bags.

15. Trash bags formed by the process of claim 14.

* * * * *